(12) United States Patent
Kano (10) Patent No.: US 10,512,453 B2
(45) Date of Patent: Dec. 24, 2019

(54) ULTRASONIC SENSOR AND ELECTRONIC DEVICE

(71) Applicant: SEIKO EPSON CORPORATION, Tokyo (JP)

(72) Inventor: Kazuyuki Kano, Aichi (JP)

(73) Assignee: Seiko Epson Corporation, Tokyo (JP)

(*) Notice: Subject to any disclaimer, the term of this patent is extended or adjusted under 35 U.S.C. 154(b) by 1059 days.

(21) Appl. No.: 14/293,351

(22) Filed: Jun. 2, 2014

(65) Prior Publication Data

US 2014/0276080 A1    Sep. 18, 2014

Related U.S. Application Data

(63) Continuation of application No. 13/093,021, filed on Apr. 25, 2011, now Pat. No. 8,771,192.

(30) Foreign Application Priority Data

Apr. 27, 2010    (JP) .................... 2010-101774

(51) Int. Cl.
| | | |
|---|---|---|
| A61B 8/14 | (2006.01) | |
| A61B 8/08 | (2006.01) | |
| A61B 8/06 | (2006.01) | |
| A61B 8/00 | (2006.01) | |
| B06B 1/06 | (2006.01) | |
| G10K 11/00 | (2006.01) | |
| G01S 15/89 | (2006.01) | |
| A61B 8/02 | (2006.01) | |
| A61B 8/04 | (2006.01) | |

(52) U.S. Cl.
CPC .............. *A61B 8/5269* (2013.01); *A61B 8/02* (2013.01); *A61B 8/04* (2013.01); *A61B 8/06* (2013.01); *A61B 8/42* (2013.01); *A61B 8/4227* (2013.01); *A61B 8/4455* (2013.01); *A61B 8/56* (2013.01); *B06B 1/0629* (2013.01); *G01S 15/8915* (2013.01); *G10K 11/004* (2013.01)

(58) Field of Classification Search
CPC ...................................................... A61B 8/00
See application file for complete search history.

(56) References Cited

U.S. PATENT DOCUMENTS

| 3,949,240 A | 4/1976 | Saito et al. |
| 2002/0007118 A1 | 1/2002 | Adachi et al. |

(Continued)

FOREIGN PATENT DOCUMENTS

| JP | 2001-258879 A | 9/2001 |
| JP | 2009-225419 A | 10/2009 |

*Primary Examiner* — Joel F Brutus
(74) *Attorney, Agent, or Firm* — Global IP Counselors, LLP (57) ABSTRACT

The ultrasonic sensor includes, on the same substrate, transmitter elements, receiver elements, a potential controller for receiver electrodes of the receiver elements, and a connection switching unit for the receiver electrodes and the potential controller. During the ultrasound transmission period of the transmitter elements, the connection switching unit connects the potential controller and one of the receiver electrodes, and connects the receiver electrodes. During the reception period of the receiver elements, the connection switching unit disconnects the potential controller and the one of the receiver electrodes, and disconnects the receiver electrodes.

6 Claims, 6 Drawing Sheets

(56) References Cited

U.S. PATENT DOCUMENTS

| | | | |
|---|---|---|---|
| 2002/0045829 A1* | 4/2002 | Nakamura | A61B 5/02438 600/454 |
| 2003/0012693 A1* | 1/2003 | Otillar | B01J 19/0046 506/39 |
| 2005/0096554 A1* | 5/2005 | Dudik | A61B 5/6806 600/500 |
| 2006/0043843 A1* | 3/2006 | Sugiura | B06B 1/0629 310/348 |
| 2006/0208612 A1* | 9/2006 | Takayama | H01H 57/00 310/311 |
| 2006/0241467 A1 | 10/2006 | Takeda et al. | |
| 2009/0001853 A1* | 1/2009 | Adachi | A61B 8/4483 310/323.19 |
| 2009/0079684 A1 | 3/2009 | Watanabe | |
| 2009/0168603 A1 | 7/2009 | Okuda et al. | |
| 2009/0236949 A1* | 9/2009 | Fujii | C23C 14/088 310/367 |

* cited by examiner

ULTRASONIC SENSOR AND ELECTRONIC DEVICE

CROSS-REFERENCE TO RELATED APPLICATIONS

This is a continuation application of U.S. patent application Ser. No. 13/093,021 filed on Apr. 25, 2011. This application claims priority to Japanese Patent Application No. 2010-101774 filed on Apr. 27, 2010. The entire disclosures of U.S. patent application Ser. No. 13/093,021 and Japanese Patent Application No. 2010-101774 are hereby incorporated herein by reference.

BACKGROUND

Technical Field

The present invention relates to an ultrasonic sensor and to an electronic device.

Related Art

One type of ultrasonic sensor known in the prior art has a transmitter element for transmitting ultrasonic waves to a detection subject, and receiver elements for receiving ultrasonic waves reflected from the detection subject, the elements being disposed in an array on the same substrate (see Japanese Laid-Open Patent Application Publication No. 2009-225419, for example).

The ultrasonic sensor disclosed in Japanese Laid-Open Patent Application Publication No. 2009-225419 is provided with an oscillation isolation member for compartmentalizing the transmitter element which transmits ultrasonic waves, and the receiver elements which receive ultrasonic waves. This oscillation isolation member serves to inhibit transmission of oscillation from the transmitter element to the receiver elements during ultrasound transmission, and to reduce reception of oscillation noise by the receiver elements.

SUMMARY

According to the ultrasonic sensor disclosed in Japanese Laid-Open Patent Application Publication No. 2009-225419, oscillation noise of the transmitter element is reduced by the oscillation isolation member. However, because oscillation of the transmitter element during ultrasound transmission is greater than oscillation of the receiver elements during ultrasonic wave reception, oscillation noise cannot be eliminated to a sufficient extent, and the resultant problem is diminished sensing accuracy of the received signal.

Specifically, in an ultrasonic sensor, when ultrasound is output from a transmitter element and the ultrasound that is reflected by an object such as a detection subject is subsequently input to a receiver element, the ultrasound experiences attenuation and reduced sound pressure with greater distance from the transmitter element to the object and greater distance from the object back to the receiver element. Such attenuation of ultrasound and reduced sound pressure is observed in reflection by objects as well. Thus, the ultrasound input to the receiver element will have lower sound pressure as compared with the ultrasound that was output by the transmitter element, and for this reason it is typical practice to connect an amplifier to the receiver element, and to detect the received signal based on ultrasound input to the receiver element once the signal has been amplified by the amplifier.

Consequently, despite reduced oscillation transmission from the transmitter element through the use of an oscillation isolation member, if even slight oscillation reaches the receiver element, the signal produced by the oscillation will be amplified and detected as oscillation noise. For this reason, it was difficult to distinguish between oscillation noise and a received signal produced by ultrasound reflected by an object, resulting in diminished sensing accuracy of received signals.

It is accordingly an object of the present invention to provide an ultrasonic sensor and an electronic device able to afford reduced detection of oscillation noise of the transmitter element and enhanced sensing accuracy of received signals.

An ultrasonic sensor according to one aspect includes a substrate, a transmitter element, a receiver element, a potential controller, a receiver amplifier, a potential control switch, and a short switch. The transmitter element is formed above the substrate. The transmitter element includes an transmission film adapted to transmit ultrasound through oscillation, a transmission piezoelectric body for causing the transmission film to oscillate, and a pair of actuation electrodes for applying an actuation voltage to the transmission piezoelectric body. The receiver element is formed above the substrate. The receiver element includes a reception film adapted to oscillate through reception of the ultrasound, a reception piezoelectric body for converting oscillation of the reception film to an electrical signal, and a pair of receiver electrodes for picking up the electrical signal that is output from the reception piezoelectric body. The potential controller is configured to apply a first potential to one of the receiver electrodes. The first potential is negative voltage. The receiver amplifier is connected to each of the receiver electrodes. The potential control switch is configured to switch a state of connection between the one of the receiver electrodes and the potential controller. The short switch is connected to each of the receiver electrodes and configured to switch a state of connection between the receiver electrodes. During a transmission period in which the ultrasound is transmitted by the transmitter element, the potential control switch is configured to switch to a connection state in which the potential controller and the one of the receiver electrodes are connected, and the short switch is configured to switch to a connection state in which the receiver electrodes are connected. During a reception period in which the ultrasound is received by the reception element, the potential control switch is configured to switch to a disconnected state in which the potential controller and the one of the receiver electrodes are disconnected, and the short switch is configured to switch to a disconnected state in which the receiver electrodes are disconnected.

BRIEF DESCRIPTION OF THE DRAWINGS

Referring now to the attached drawings which form a part of this original disclosure.

DETAILED DESCRIPTION OF EXEMPLARY EMBODIMENTS

First Embodiment

A first embodiment of the present invention is described below with reference to the drawings.

Configuration of Biological Testing Device

Figure 1:
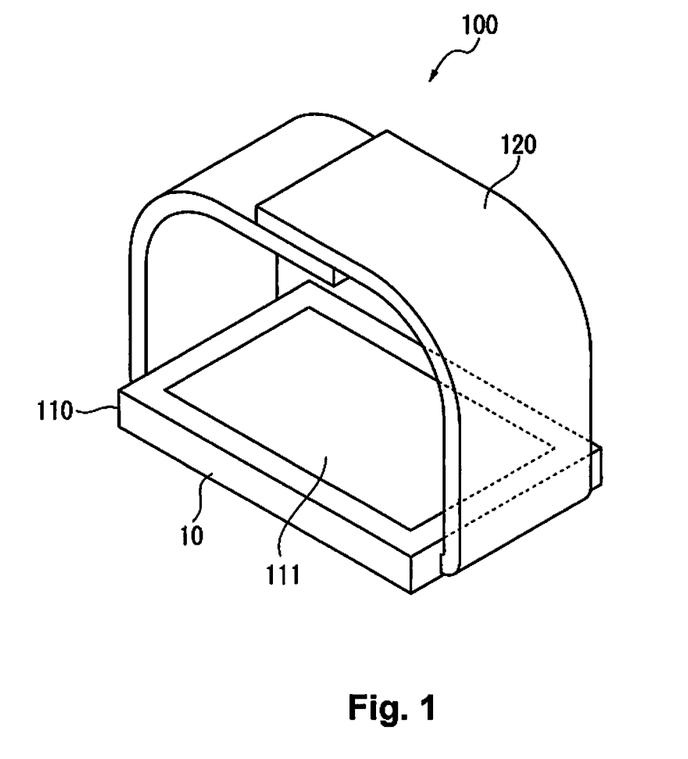
FIG. 1 is an exterior view of a biological testing device according to a first embodiment of the invention.

FIG. 1 is an exterior view showing a biological testing device 100 as an electronic device according to a first embodiment of the invention.

As shown in FIG. 1, the biological testing device 100 is a device designed to attach to a human finger using a band 120. The biological testing device 100 includes a device main unit 110, and the band 120 which is used to attach the device main unit 110 to the finger. The biological testing device 100 is also provided with an ultrasonic sensor 10.

This biological testing device 100 is designed, for example, to be arranged with the finger contacting a contact surface 111, and to transmit ultrasound to the finger from the ultrasonic sensor 10 as well as to receive ultrasound that is reflected from biological structures, such as blood vessels inside the finger, for example, for the purpose of testing blood flow conditions, such as pulse or blood pressure, for example, or to test some other biological condition.

Configuration of Ultrasonic Sensor

Figure 2:
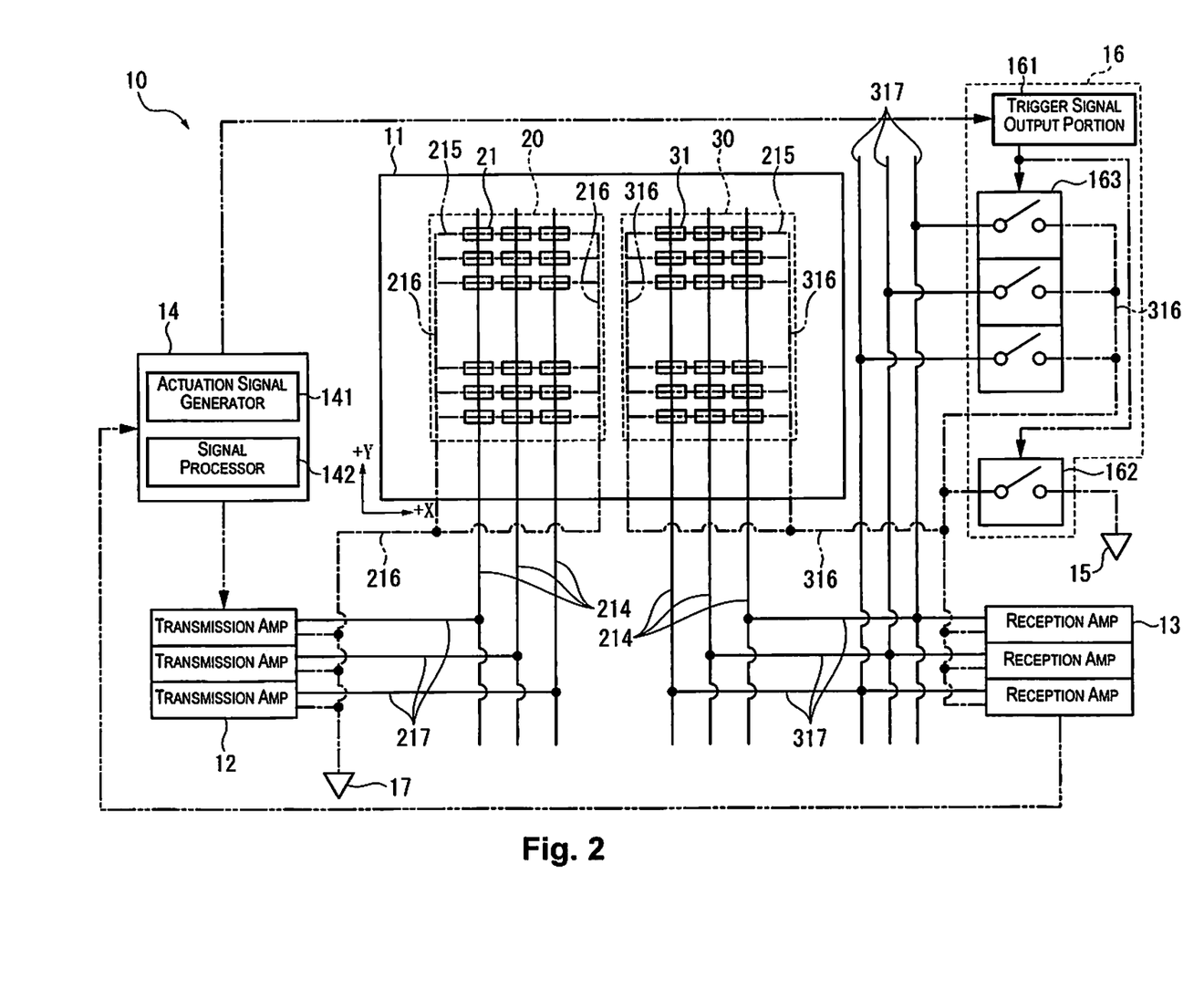
FIG. 2 is a circuit block diagram depicting in model form an ultrasonic sensor in the first embodiment.

FIG. 2 is a circuit block diagram depicting in model form the ultrasonic sensor 10 in the first embodiment.

The ultrasonic sensor 10 is designed to transmit ultrasound to the finger, as well as to receive ultrasound reflected from biological structures such as blood vessels inside the finger, for example.

As shown in FIG. 2, the ultrasonic sensor 10 has a transmitter array 20 and a receiver array 30 adjacent to the transmission array 20.

The transmitter array 20 is made up of an array structure in which a plurality of transmitter elements 21 are arranged along the horizontal direction (the X axis direction in FIG. 2) and the vertical direction (the Y axis direction in FIG. 2). The receiver array 30 is made up of an array structure in which a plurality of receiver elements 31 are arranged along the horizontal direction and the vertical direction.

The transmitter elements 21 are elements adapted to transmit ultrasound on the basis of a transmission signal (actuating signal) that is input from an actuation controller 14, discussed later. The receiver elements 31 are elements adapted to receive ultrasound reflected from a detection subject or the like, and to convert ultrasound to an electrical signal for output to the actuation controller 14.

According to the example shown here in FIG. 2, the ultrasonic sensor 10 of the present embodiment has a configuration in which the plurality of transmitter elements 21 and the plurality of receiver elements 31 are formed on a single sensor array substrate 11; however, this arrangement is not limiting. For example, in another possible arrangement, the transmitter array 20 and the receiver array 30 have respective sensor array substrates, and these sensor array substrates are fastened onto a single sensor array substrate.

The sensor array substrate 11 is formed with generally rectangular shape, and is made of semiconductor-forming material such as silicon (Si), for example.

In addition to the arrays 20, 30, the ultrasonic sensor 10 is provided with transmission amps 12 for amplifying the actuating signal which is input to the transmitter elements 21; reception amps 13 for amplifying the received ultrasound signal received by the receiver elements 31; the actuation controller 14, which controls operation of the ultrasonic sensor 10; a potential controller 15 adapted to bring receiver electrodes 3132, 3133 (described later) of the receiver elements 31 to a first potential during a trigger output period Tr (see FIG. 4); and a connection switching unit 16 for switching the connection state between the potential controller 15 and the receiver electrodes 3132, 3133.

Configuration of Transmitter Elements

Figure 3:
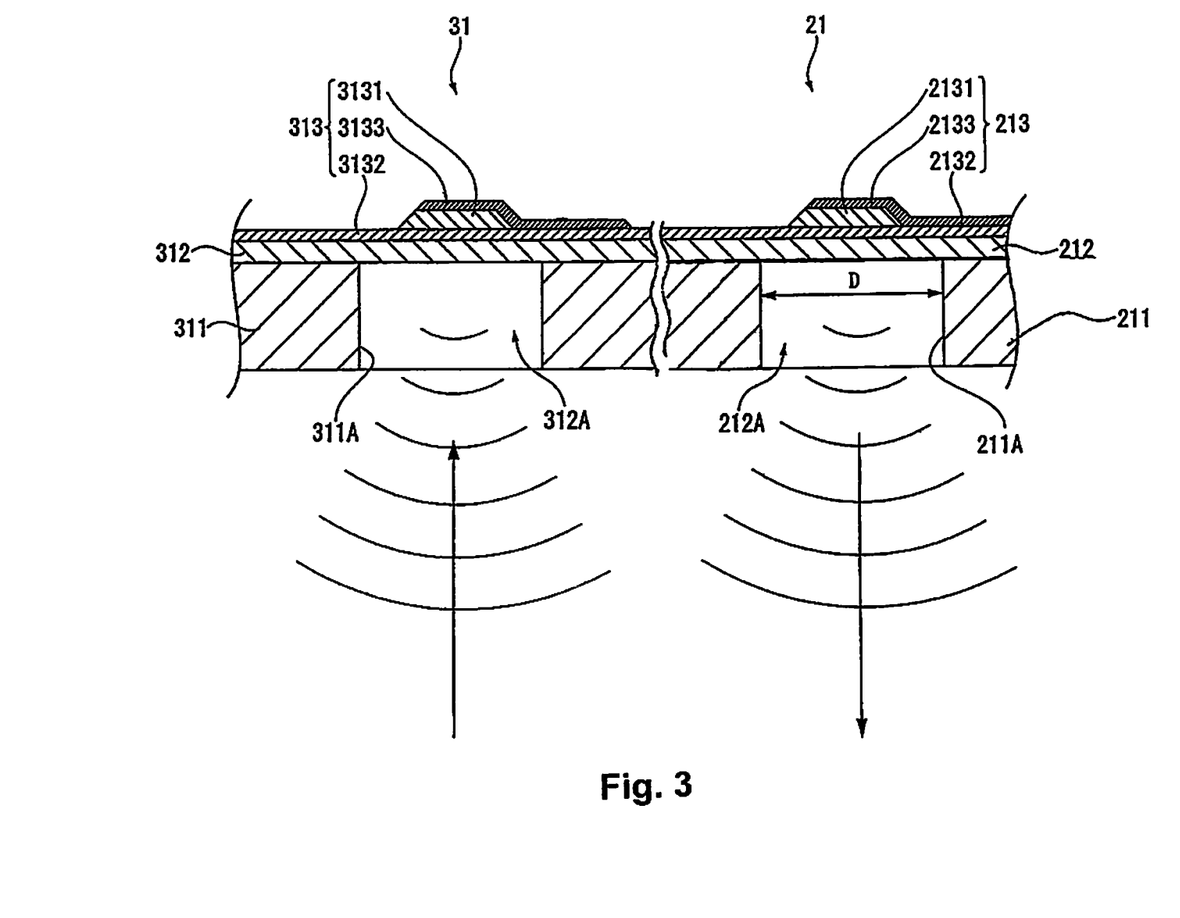
FIG. 3 is a cross sectional view of a transmitter element and a receiver element in the first embodiment.

FIG. 3 is a cross sectional view depicting in model form a transmitter element 21 and a receiver element 31 taken in cross section along the thickness direction of the sensor array substrate 11. In the drawing view of FIG. 3, the transmitter element 21 is shown at right in the drawing. As shown in FIG. 3, the transmitter element 21 is provided with a support portion 211, a support film 212, and a transmission piezoelectric body 213.

The support portion 211 is a section that is formed at the location where the transmitter element 21 is positioned on the sensor array substrate 11. In this support portion 211 there is formed an opening portion 211A having, for example, a rectangular shape in plan view when the sensor array substrate 11 is viewed from a direction perpendicular to the plane of the sensor array substrate 11 (sensor plan view).

The diameter dimension D of the opening portion 211A is selected appropriately within a range of about 100 μm to 200 μm, for example, depending on the natural frequency of a diaphragm 212A (transmission film), discussed later. Ultrasound produced through oscillation of this diaphragm 212A is directed out towards the opening portion 211A.

The support film 212 obstructs the opening portion 211A. In the present embodiment, this support film 212 is formed with a two-layer configuration. For example, where the support portion 211 is an Si substrate, an $SiO_2$ layer having a thickness dimension of 3 μm is produced on the support portion 211 by a thermal oxidation process. Then, using a method such as sputtering or vapor deposition, a $ZrO_2$ layer having a thickness dimension of 400 nm is produced over the $SiO_2$ layer to form two layers.

The section where the opening portion 211A is obstructed by the support film 212 constitutes the diaphragm 212A. The diaphragm 212A is a member of thin film form, and through the opening portion 211A formed in the support portion 211 lies exposed to a space in the ultrasound output direction of the transmitter element 21 (in FIG. 3, downward in the plane of the page).

Similar to the opening portion 211A, the transmission piezoelectric body 213 is a film-like member of rectangular shape in sensor plan view, for example. This transmission piezoelectric body 213 is provided with a piezoelectric film 2131, and with actuation electrodes (a lower electrode 2132 and an upper electrode 2133) for applying voltage to the piezoelectric film 2131.

The piezoelectric film 2131 is a film of PZT formed with a thickness dimension of 1.4 μm, for example. According to the present embodiment, PZT is employed for the piezoelectric film 2131; however, any material able to expand and contract in an in-plane direction through the application of electrical voltage may be used. Examples include lead titanate ($PbTiO_3$), lead zirconate ($PbZrO_3$), or lead lanthanum titanate ($(Pb,La)TiO_3$).

The lower electrode 2132 and the upper electrode 2133 are electrodes disposed sandwiching the piezoelectric film 2131; the upper electrode 2132 is formed with a thickness dimension of 200 nm on the face of the piezoelectric film 2131 facing towards the diaphragm 212A, while the upper electrode 2133 is formed with a thickness dimension of 50 nm on the back face side of the piezoelectric film 2131, i.e., side opposite the face that faces towards the diaphragm 212A.

The upper electrodes 2133 and the lower electrodes 2132 of the transmitter elements 21 apply a designated voltage to the piezoelectric film 2131 in response to an actuating signal input from the actuation controller 14.

Lower electrode lines 214 extending along the Y axis direction of the sensor array substrate 11 connect to the lower electrodes 2132, as shown in FIG. 2. Upper electrode lines 215 extending along the X axis direction of the sensor array substrate 11 connect to the upper electrodes 2133.

In this transmitter element 21, the piezoelectric film 2131 expands and contracts in an in-plane direction through application of voltage across the lower electrode 2132 and the upper electrode 2133. At this time, one of the faces of the piezoelectric film 2131 is joined to the diaphragm 212A via the lower electrode 2132, the upper electrode 2133 is formed on the other face, and no additional layers are stacked over this upper electrode 2133. For this reason, the piezoelectric film 2131 readily expands and contracts on the upper electrode 2133 side, but expands and contracts only with difficulty on the diaphragm 212A side. Therefore, when voltage is applied to the piezoelectric film 2131, the film flexes into a convex shape towards the opening portion 211A, inducing flexure of the diaphragm 212A. Consequently, by applying AC voltage to the piezoelectric film 2131, the diaphragm 212A is caused to oscillate in the film thickness direction, and ultrasound is output through this oscillation of the diaphragm 212A.

Configuration of Receiver Elements

As noted previously, the receiver elements 31 have a configuration identical to that of the transmitter elements 21, and therefore a brief description of the configuration will suffice.

In the drawing view of FIG. 3, the receiver element 31 is shown at left in the drawing. This receiver element 31 is provided with a support portion 311, a support film 312, and a reception piezoelectric body 313. The reception piezoelectric body 313 is provided with a piezoelectric film 3131 and with receiver electrodes (a lower electrode 3132 as one of the receiver electrodes, and an upper electrode 3133 as the other receiver electrode) for picking up an electrical signal (received signal). The design of the receiver element 31 is such that when ultrasound reflected from a detection subject is received by a diaphragm 312A (reception film), the diaphragm 312A oscillates in the film thickness direction. In the receiver element 31, this oscillation of the diaphragm 312A gives rise to a potential difference between the face of the piezoelectric film 3131 on the lower electrode 3132 side thereof and the face on the upper electrode 3133 side thereof. A received signal which reflects the amount of displacement of the piezoelectric film 3131 is then output from the upper electrode 3133 and the lower electrode 3132 to the actuation controller 14.

Configuration of Transmitter Array

As shown in FIG. 3, in the transmitter array 20, transmitter elements 21, which are arranged along the X axis direction, have common connections to upper electrode lines 215 as described earlier, and these upper electrode lines 215 are connected to transmission common electrode lines 216 which are disposed at the X direction ends of the transmitter array 20.

Transmitter elements 21, which are arranged along the Y axis direction of the transmitter array 20, have common connections to the lower electrode lines 214, and are connected to transmission actuation electrode lines 217 which are disposed in the −Y direction of the transmitter array 20, for example. Here, because the transmitter array 20 of the present embodiment is designed such that the ultrasound scans along one direction (the X direction) while adjusting the transmission angle, the lower electrode lines 214 have common connections with the transmitter elements 21; however, in cases where ultrasound scans in a two-dimensional direction, the lower electrode lines 214 may lead out from individual transmitter elements 21.

The transmission common electrode lines 216 and the transmission actuation electrode lines 217 connect to the transmission amps 12. The transmission common electrode lines 216 are connected to ground (GND) through connection to a reference potential 17, and the upper electrodes 2133 of the transmitter elements 21 are grounded. Meanwhile, the transmission actuation electrode lines 217 input the actuation signal from the transmission amps 12 and apply an actuation voltage to the lower electrode 2132, thereby giving rise to a potential difference between the actuation electrodes 2132, 2133, and actuating the transmitter elements 21.

Configuration of Transmitter Array

As shown in FIG. 2, in the receiver array 30 as in the transmitter array 20, receiver elements 31, which are arranged along the X axis direction, have common connections to upper electrode lines 215, and these upper electrode lines 215 are connected to reception common electrode lines 316 which are disposed at the X direction ends of the receiver array 30.

Receiver elements 31, which are arranged along the Y axis direction of the receiver array 30, have common connections to the lower electrode lines 214, and are connected to reception detection electrode lines 317 which are disposed in the −Y direction of the receiver array 30, for example.

These reception common electrode lines 316 and reception detection electrode lines 317 connect to the reception amps 13. The amplitude (potential difference) of the received signal input to the reception common electrode lines 316 and the reception detection electrode lines 317 from the receiver electrodes 3132, 3133 of the receiver elements 31 is amplified by the reception amps 13 to detect the frequency and other properties of the ultrasound received by the receiver elements 31.

Configuration of Transmission Amp and Reception Amp

The transmission amps 12 amplify the voltage value of the actuation signal input from the actuation controller 14, and output the amplified actuation signal to the transmission actuation electrode lines 217.

The transmission amps 12 are connected to the transmission common electrode lines 216 (which are connected to the reference potential 17) and to the transmission actuation electrode lines 217. The reception amps 13 input from the reception detection electrode lines 317 a received signal that has been converted on the basis of the ultrasound received by the receiver elements 31, then amplify the voltage value of the received signal and output it to the actuation controller 14. The reception amps 13 are connected to the reception common electrode lines 316 and to the reception detection electrode lines 317.

Configuration of Actuation Controller

The actuation controller 14 controls the actuation signal which is input to the transmitter elements 21 of the ultrasonic sensor 10, and also processes the received signal which is output by the receiver elements 31 of the ultrasonic sensor 10. As shown in FIG. 2, this actuation controller 14 is provided with an actuation signal generator 141 and a signal processor 142.

The actuation signal generator 141 is a circuit device that generates an actuation signal for output to the transmitter elements 21, and that outputs the signal to the transmission amps 12. Once the actuation signal generator 141 outputs an actuation signal to the transmission amps 12, a trigger signal generator 161, discussed later, is activated. Specifically, the actuation signal generator 141 generates an actuation signal during individual burst cycles Tp (see FIG. 4), and outputs the actuation signal to the transmission amps 12 during a transmission period Tt (see FIG. 4).

The signal processor 142 is a circuit device for processing the received signals output by the receiver elements 21 and amplified by the reception amps 13. In the signal processor 142, pulse, blood pressure, or the like is calculated on the basis of the received signal frequency, for example.

Configuration of Connection Switching Unit

The connection switching unit 16 includes the trigger signal generator 161, a potential control switch 162, and a short switch 163. During the output interval Tr of a trigger signal which is output by the trigger signal generator 161 (see FIG. 4), the connection switching unit 16 switches to a first state in which the potential controller 15 and the receiver electrodes 3132, 3133 are connected. Once the trigger output period Tr has elapsed and the trigger signal has ceased, the connection switching unit 16 switches to a second state in which the potential controller 15 and the receiver electrodes 3132, 3133 are disconnected.

Here, in the first state, the potential controller 15 applies negative voltage to the receiver electrodes 3132, 3133 to bring them to a first potential at which the receiver electrodes 3132, 3133 are at the same potential. The potential difference of the receiver electrodes 3132, 3133 is therefore zero.

The trigger signal generator 161 is a circuit device that, once activated by the actuation signal generator 141 of the actuation controller 14, outputs a trigger signal to the potential control switch 162 and to the short switch 163. The trigger signal generator 161 has been set to output the trigger signal for a designated duration (the trigger output period Tr in FIG. 4).

Figure 4:
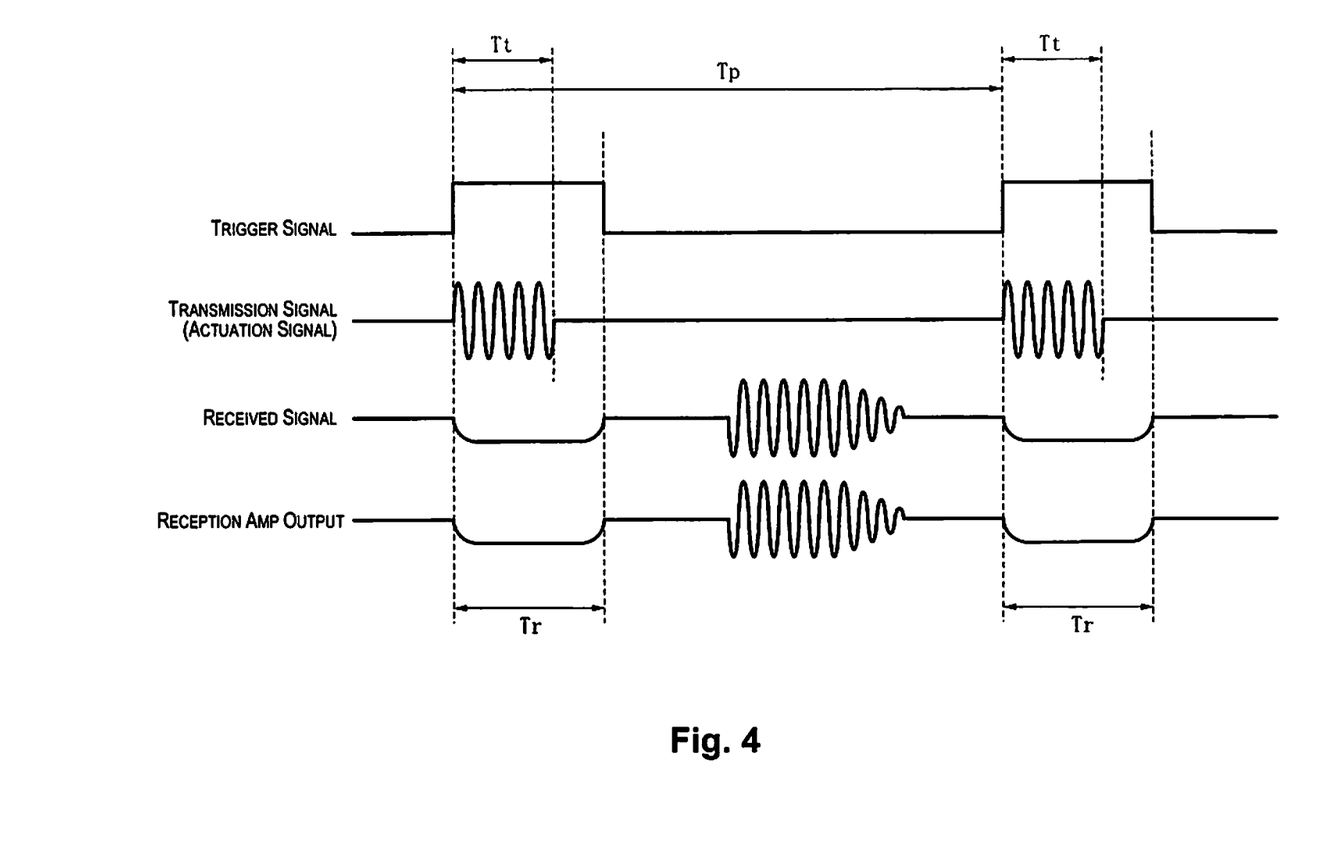
FIG. 4 is a graph showing a relationship of voltage of various signals to time in the first embodiment.

Referring to FIG. 4, optionally, the trigger output period Tr may be set to a duration longer than the transmission period Tt; specifically, set to a duration longer than the transmission period Tt by the equivalent of at least one cycle (one wavelength) of the actuation signal or more. According to the present embodiment, the trigger output period Tr is set to a duration longer than the transmission period Tt by the equivalent of approximately two cycles of the actuation signal. The upper limit for the trigger output period Tr is computed using Equation (1) below.

Equation (1)

$$Tr < 2 \times \frac{Dtr}{C} \qquad (1)$$

Here, c is the sound speed (m/s) of a medium, and Dtr is the distance (m) from the ultrasonic sensor 10 to a detection subject. This distance Dtr (m) is a designated value determined on the basis of the structure of the ultrasonic sensor 10 (the distance between the elements 21, 31 and the sensor surface), and the detection subject (in the present embodiment, blood vessels).

A micro switch or the like, for example, is employed as the potential control switch 162 which is connected to the reception common electrode lines 316 and to the potential controller 15. The potential control switch 162 is also connected to the reception common electrode lines 316.

When a trigger signal is input from the trigger signal generator 161, the potential control switch 162 switches to a first state for connecting the potential controller 15 and the reception common electrode lines 316. Thereby, negative voltage is applied to the upper electrodes 3133 from the potential controller 15 via the reception common electrode lines 316.

On the other hand, when input of the trigger signal ceases, the potential control switch 162 switches to a second state for severing the connection of the potential controller 15 and the reception common electrode lines 316. Thereby, negative voltage ceases to be applied to the upper electrodes 3133.

Similar to the potential control switch 162, the short switch 163 may employ, for example, a micro switch or the like which is connected to the reception common electrode lines 316 and the reception detection electrode lines 317. The electrode lines 316, 317 are connected to the receiver electrodes 3132, 3133 and to the reception amps 13.

When a trigger signal is input from the trigger signal generator 161, the short switch 163 assumes a connection state for connecting the reception common electrode lines 316 and the reception detection electrode lines 317. The receiver electrodes 3132, 3133 are shorted thereby. As mentioned previously, the potential control switch 162 applies negative voltage from the potential controller 15 to the upper electrodes 3133 via the reception common electrode lines 316. Therefore, negative voltage from the potential controller 15 flows into the reception detection electrode lines 317 via the reception common electrode lines 316 and the short switch 163, and applied to the lower electrodes 3132.

The receiver electrodes 3132, 3133 are thereby brought to a first potential at which they have the same potential, and the potential difference of the receiver electrodes 3132, 3133 is zero.

Once the trigger signal ceases, the short switch 163 assumes a second state for severing the connection of the reception common electrode lines 316 and the reception detection electrode lines 317. Therefore, application of negative voltage to the lower electrodes 3132 ceases.

Operation of Ultrasonic Sensor

Figure 5:
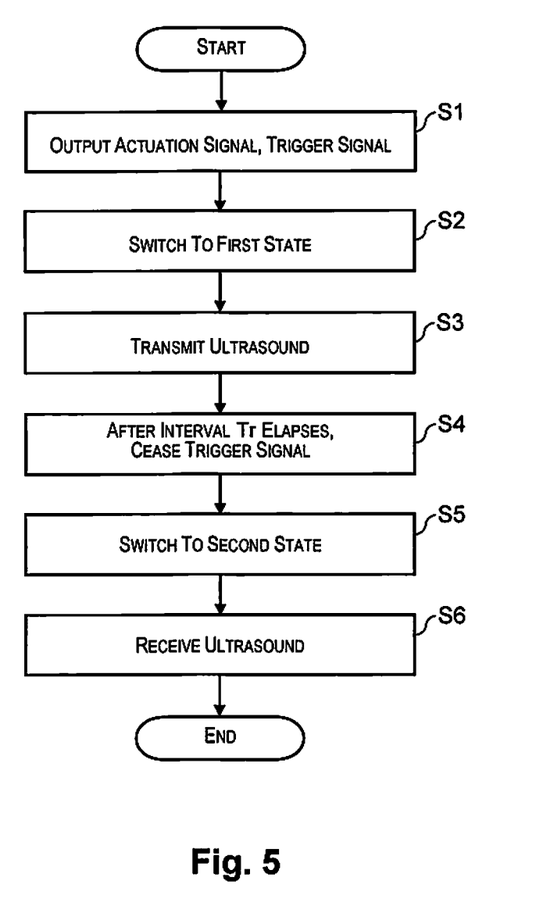
FIG. 5 is a flowchart depicting operation of the ultrasonic sensor in the first embodiment.

Operation of the ultrasonic sensor 10 is now described with reference to the graph, shown in FIG. 4, depicting the relationship of voltage values of the various signals with time, and to the flowchart shown in FIG. 5.

First, the signal generator 141 of the actuation controller 14 generates an actuation signal for output to the transmitter elements 21, and during the transmission period Tt outputs the actuation signal to the transmission amps 12 and activates the trigger signal generator 161. Thereby, during the trigger output period Tr, the trigger signal generator 161 outputs a trigger signal to the potential control switch 162 and to the short switch 163 (Step S1).

Then, once the potential control switch 162 and the short switch 163 input the trigger signal from the trigger signal generator 161, the switches assume the first state whereby negative voltage is supplied from the potential controller 15 to the reception common electrode lines 316 and the reception detection electrode lines 317, and the receiver electrodes 3132, 3133 assume a first potential at the same potential (Step S2).

Meanwhile, upon input of the actuation signal, the reception amps 12 amplify the voltage value of the actuation signal, present the actuation signal to the transmission actuation electrode lines 217, and apply actuation voltage to the lower electrodes 2132 of the transmitter elements 21 via the lower electrode lines 214. The upper electrodes 2133 of the transmitter elements 21 are grounded through connection to the reference voltage 17 via the transmission common electrode lines 216. The transmitter elements 21 are thereby actuated through generation of a potential difference between the actuation electrodes 2132, 2133, and transmit ultrasound (Step S3).

At this time, in the receiver array 30, negative voltage from the potential controller 15 is supplied to the upper electrode lines 215 and the lower electrode lines 214 via the reception common electrode lines 316 and the reception detection electrode lines 317. Therefore, the receiver electrodes 3132, 3133 of the receiver elements 31 assume a first potential at the same potential, whereby their potential difference is zero and the receiver elements 31 do not output a received signal. Specifically, as shown by the graph in FIG. 4, during trigger output periods Tr, negative voltage is applied to the receiver electrodes 3132, 3133 of the receiver elements 31 and their potential difference goes to zero, and therefore a drop is observed in the graph. Consequently, even if oscillation of the diaphragm 212A reaches the receiver elements 31 during transmission of ultrasound by the transmitter elements 21, there is no flow of current to the reception common electrode lines 316 and the reception detection electrode lines 317. Therefore, the received signal is not amplified by the reception amps 13, and output voltage is low.

Then, when the trigger output period Tr has elapsed, the trigger signal generator 161 ceases outputting the trigger signal (Step S4).

Once output of the trigger signal ceases in Step S4, the potential control switch 162 and the short switch 163 assume a second state in which their connection to the potential controller 15 is severed (Step S5).

At this time, because negative voltage from the potential controller 15 is no longer supplied to the reception common electrode lines 316 and the reception detection electrode lines 317, the receiver electrodes 3132, 3133 assume a state in which a potential difference has arisen. Therefore, a received signal from the receiver electrodes 3132, 3133 reflecting the amount of displacement of the piezoelectric film 3131 is input to the reception amps 13 from the reception common electrode lines 316 and the reception detection electrode lines 317. Then, as shown in the graph in FIG. 4, the reception amps 13 amplify the voltage value of the received signal.

The received signal that was amplified by the reception amps 13 is then input to the signal processor 142 of the actuation controller 14, whereupon the signal processor 142 performs signal processing of the received signal (Step S6). Thereby, in the signal processor 142, the amplitude, frequency, and other properties of the ultrasound received by the receiver elements 31 are detected, and pulse, blood pressure, or the like is computed.

The ultrasonic sensor 10 of the first embodiment described above affords the following advantages.

(1) During the transmission period Tt in which the transmitter elements 21 transmit ultrasound, the connection switching unit 16 switches to the first state. The paired receiver electrodes 3132, 3133 and the potential controller 15 are connected thereby, and the paired receiver electrodes 3132, 3133 are brought to a first potential at the same respective potential. Therefore, the potential difference of the paired receiver electrodes 3132, 3133 is zero, and no electrical signal is output by the paired receiver electrodes 3132, 3133. Due to this design, during the interval that the transmitter elements 21 are transmitting ultrasound, i.e., during the oscillation interval of the diaphragm 212A of the transmitter elements 21, no electrical signal is output by the paired receiver electrodes 3132, 3133 even if oscillation noise from the transmitter elements 21 reaches the receiver elements 31. Consequently, oscillation noise produced by oscillation of the transmitter elements 21 is not detected.

On the other hand, during the reception period that follows elapse of the transmission period Tt, the connection switching unit 16 switches to the second mode. Owing to this feature, the receiver elements 31 can only receive ultrasound received signals, and the sensing accuracy of the ultrasonic received signal can be enhanced.

(2) During the ultrasound transmission period Tt, the paired receiver electrodes 3132, 3133 and the potential controller 15 are connected, the potential difference of the paired receiver electrodes 3132, 3133 is zero, and no electrical signal is output by the paired receiver electrodes 3132, 3133. Specifically, no signal resulting from oscillation noise is input to the reception amps 13, thereby preventing a rise in output voltage due to amplification of oscillation noise. Consequently, power consumption by the reception amps 13 can be reduced.

(3) During the transmission period Tt, the short switch 163 is prompted to short the paired receiver electrodes 3132, 3133, and additionally the potential control switch 162 is prompted to connect the potential controller 15 and the paired receiver electrodes 3132, 3133, whereby the potential controller 15 brings the paired receiver electrodes 3132, 3133 to a first potential at the same respective potential. The potential difference of the paired receiver electrodes 3132, 3133 is therefore zero. That is, because it suffices to merely short the paired receiver electrodes 3132, 3133, the configuration can be simplified.

(4) The actuation controller 14 outputs an actuation signal for application to the paired receiver electrodes 2132, 2133 of the transmitter elements 21, and simultaneously activates the trigger signal generator 161. The trigger signal generator 161 thereby outputs a trigger signal. When the connection switching unit 16 inputs the trigger signal, it switches to the first state; and when input of the trigger signal ends, it switches to the second state. Owing to this feature, during output of the actuation signal to the transmitter elements 21 by the actuation controller 14, the connection switching unit 16 can be reliably switched to the first state, and the potential difference of the paired receiver electrodes 3132, 3133 can be brought to zero. Consequently, during the transmission period Tt, no electrical signal is output from the receiver electrodes 3132, 3133, and oscillation noise generated by oscillation of the transmitter elements 21 is not detected. Further, during the reception period following completion of the transmission period Tt, as described previously, the receiver elements 31 are able to receive only ultrasound received signals, and the sensing accuracy of the ultrasonic received signal can be enhanced.

(5) The trigger output period Tr is set to an interval of duration equivalent to at least one cycle of the ultrasonic actuation signal transmitted from the transmitter elements 21, plus the transmission period Tt.

There are instances in which oscillation noise generated during the ultrasound transmission period Tt reaches the receiver elements 31 after the transmission period has elapsed Tt. According to the present embodiment, the trigger signal continues to be output even after the transmission period Tt has elapsed, and the potential difference of the paired receiver electrodes 3132, 3133 remains at zero, whereby even if oscillation noise reaches the receiver elements 31 after the transmission period Tt has elapsed, the receiver elements 31 do not output the oscillation noise as a received signal. Consequently, the sensing accuracy of the ultrasonic received signal by the receiver elements 31 can be enhanced.

(6) The biological testing device 100 provided with the ultrasonic sensor 10 described above is disposed with the contact surface 111 contacting the finger or the like, whereupon ultrasound is transmitted to blood vessels. In this case, the contact surface 111 and the blood vessels are in mutually proximate locations. Where the detection subject is situated at a location close to the ultrasonic sensor 10 in this way, by shortening the trigger output period Tr, rapid switching between the first state and the second state can take place, and sensing of the detection subject close by is possible.

Second Embodiment

Figure 6:
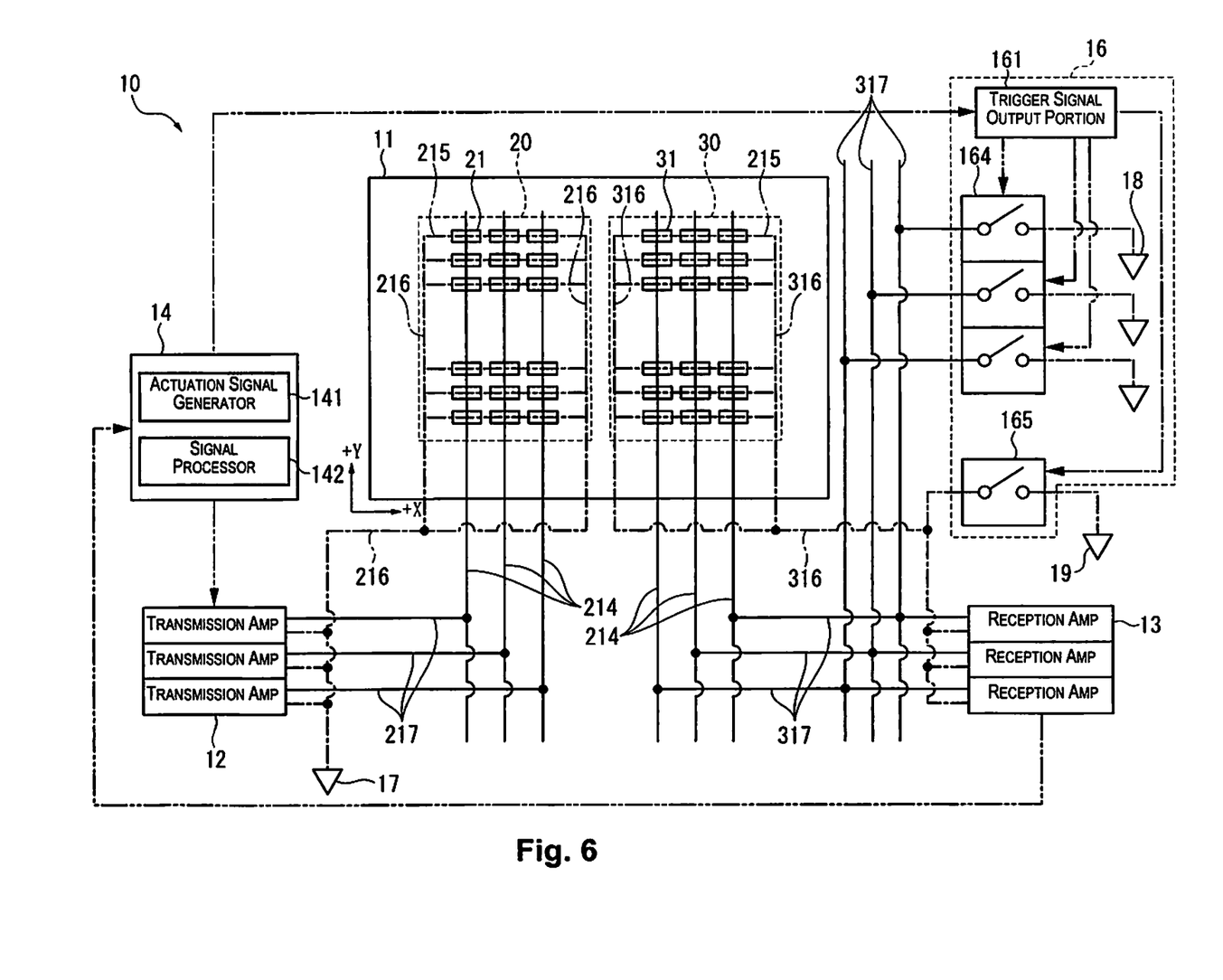
FIG. 6 is a circuit block diagram depicting in model form an ultrasonic sensor in a second embodiment.

FIG. 6 is a circuit block diagram depicting in model form an ultrasonic sensor 10 in a second embodiment.

The differences are that, whereas according to the preceding first embodiment, the connection switching unit 16 has a configuration provided with the potential control switch 162 and the short switch 163, the potential controller 16 according to the second embodiment is provided with a first switch 164 and a second switch 165 in place of the short switch 163; and the potential controller 15 is provided with a first potential controller 18 and a second potential controller 19 respectively connected to the first switch 164 and the second switch 165.

The first switch 164 has a configuration comparable to the potential control switch 162 in the preceding embodiment, and is adapted to switch the connection state of the first potential controller 18 and the reception detection electrode lines 317 connected to the lower electrodes 3132.

The second switch 165 has a configuration comparable to the potential control switch 162 in the preceding embodiment, and is adapted to switch the connection state of the second potential controller 19 and the reception common electrode lines 316 connected to the upper electrodes 3133.

The first potential controller 18 applies negative voltage to the lower electrodes 3132, while the second potential controller 19 applies negative voltage to the upper electrodes 3133.

Input of a trigger signal from the trigger signal generator 161 sets up a first state in which the first switch 164 connects the first potential controller 18 with the reception detection electrode lines 317, and the second switch 165 connects the second potential controller 19 with the reception common electrode lines 316. This sets up a state in which negative voltage is applied to the paired receiver electrodes 3132, 3133 from the potential controllers 18, 19. The paired receiver electrodes 3132, 3133 are thereby brought to a first potential at the same potential, and the potential difference of the paired receiver electrodes 3132, 3133 is zero.

On the other hand, when input of the trigger signal ceases, the first switch 164 and the second switch 165 assume a second state in which the first potential controller 18 is disconnected from the reception detection electrode lines 317, and the second potential controller 19 is disconnected from the reception common electrode lines 316. As a result, negative voltage ceases to be applied to the paired receiver electrodes 3132, 3133.

The second embodiment described above affords advantages comparable to advantages (1), (2), and (4) to (6) of the preceding first embodiment.

Additionally, in the present embodiment, during the transmission period Tt the connection switching unit 16 switches the first switch 164 to a connection state for connecting the lower electrodes 3132 to the first potential controller 18, and additionally switches the second switch 165 to a connection state for connecting the upper electrodes 3133 to the second potential controller 19. The paired receiver electrodes 3132, 3133 are thereby connected with the first and second potential controllers 18, 19, and the paired receiver electrodes 3132, 3133 are respectively brought to the same potential at a first potential. Therefore, the potential difference of the paired receiver electrodes 3132, 3133 is zero, and no electrical signal is output from the receiver electrodes 3132, 3133. Owing to this feature, during the oscillation interval of the diaphragm 212A of the transmitter elements 21, no electrical signal is output from the paired receiver electrodes 3132, 3133 even if oscillation noise from the transmitter elements reaches the receiver elements 31. Consequently, oscillation noise generated by oscillation of the transmitter elements 21 is not detected.

On the other hand, during the reception period following elapse of the transmission period Tt, as described previously, the connection switching unit 16 switches to the second state. The receiver elements 31 thereby can receive only ultrasound received signals, and the sensing accuracy of the ultrasonic received signal can be enhanced.

Modifications of the Embodiments

While certain preferred configurations, methods, and the like for embodying the present invention have been shown herein, these are not intended as limiting of the invention.

In the preceding embodiments, negative voltage is applied to the paired receiver electrodes 3132, 3133 from the potential controllers 15, 18, 19 to bring the paired receiver electrodes 3132, 3133 to a first potential; however, optionally, the potential controllers 15, 18, 19 may be set to reference potential, and the paired receiver electrodes 3132, 3133 brought to the first potential by being grounded.

In this case, the configuration may omit the potential control switch 162 of the first embodiment, and keep the upper electrodes 3133 grounded at all times to the potential controller 15. Likewise, in the second embodiment, the configuration may omit the second switch 165, and keep the upper electrodes 3133 grounded at all times to the second potential controller 19. This affords a configuration in which only the short switch and the first switch 164 are controlled, and the configuration can be simplified.

In the preceding embodiments, the trigger signal is output during the trigger output period Tr; however, optionally, transmission may take place during the transmission period Tt only, or the duration of the trigger output period Tr may be set appropriately depending on the distance to the detection subject.

In the preceding embodiments, the actuation controller 14 and the connection switching unit 16 are configured separately, but a configuration incorporating the actuation controller 14 into the connection switching unit 16 is also possible. With this configuration, the trigger signal generator 161 will output a trigger signal once the actuation signal generator 141 generates an actuation signal, and the response of the trigger signal generator 161 can be improved. Also, while the trigger signal generator 161 is part of the connection switching unit 16, optionally, it may be part of the actuation controller 14 instead. In yet another possible configuration, the trigger signal generator 161 is omitted, and a trigger signal is generated during generation of the actuation signal by the actuation signal generator 141.

While preceding embodiments describe an example of a biological testing device as the electronic device, no limitation thereto is imposed; for example, devices adapted to sense distance between vehicles, or devices for measuring flow rate or flow speed of a fluid through piping, and the like may also be given as examples.

An ultrasonic sensor according to the illustrate embodiment has, on the same substrate, a transmitter element, which includes an transmission film adapted to transmit ultrasound through oscillation, a transmission piezoelectric body for causing the transmission film to oscillate, and a pair of actuation electrodes for applying an actuation voltage to the transmission piezoelectric body; and a receiver element including a reception film adapted to oscillate through reception of the ultrasound, a reception piezoelectric body for converting oscillation of the reception film to an electrical signal, and a pair of receiver electrodes for picking up the electrical signal that is output from the reception piezoelectric body. The ultrasonic sensor includes a potential controller configured to bring the receiver electrodes to a first potential, and a connection switching unit configured to switch a connection state of the receiver electrodes and the potential controller. During the transmission period in which the ultrasound is transmitted by the transmitter element, the connection switching unit being configured to switch to a first state in which the potential controller and the receiver electrodes are connected. During the reception period in which the ultrasound is received by the reception element, the connection switching unit being configured to switch to a second state in which the potential controller and the receiver electrodes are disconnected.

According to this ultrasonic sensor, when actuation voltage is applied from the actuation electrodes to the transmission piezoelectric body in the transmitter element, the transmission film oscillates due to expansion and contraction of the transmission piezoelectric body, and ultrasound is transmitted from the transmission film. In the receiver element, ultrasound reflected from a detection subject is received by the reception film, whereby the reception film oscillates. A potential difference is thereby created in the reception piezoelectric body, and an electrical signal based on the potential difference is output from the paired receiver electrodes.

According to this embodiment, during the transmission period in which ultrasound is transmitted by the transmitter elements, the connection switching unit switches to a first state. The paired receiver electrodes and the potential controller are connected thereby, whereby the paired receiver electrodes are respectively brought to the same potential at a first potential. Therefore, the potential difference of the paired receiver electrodes is zero, and the receiver electrodes do not output an electrical signal. By so doing, during intervals of transmission of ultrasound by the transmitter elements, specifically, during intervals in which the transmission film of the transmitter elements is oscillating, no electrical signal is output from the receiver electrodes even if oscillation noise from the transmitter elements reaches the receiver elements. Consequently, oscillation noise produced by oscillation of the transmitter elements is not detected.

During the reception period following completion of a transmission period, on the other hand, the connection switching unit switches to the second state. Therefore, the receiver elements can receive only the ultrasound received signals, and the sensing accuracy of the ultrasonic received signal can be enhanced.

As mentioned previously, in typical practice, an amplifier is connected to the receiver element, and received signals based on ultrasound input to the receiver element are detected after amplification by the amplifier. Oscillation noise generated by oscillation of the transmission film of the transmitter element has amplitude several tens or several hundreds of times greater than ultrasonic received signals input to the receiver element. Therefore, if oscillation noise is input to the amplifier, there is a risk of increased output voltage of the amplifier due to the amplified oscillation noise, resulting in increased energy consumption.

According to this embodiment, during ultrasound transmission periods, the paired receiver electrodes and the potential controller are connected, the potential difference of the paired receiver electrodes is zero, and no electrical signal is output by the receiver electrodes. Specifically, because the signal produced by oscillation noise is not input to the amplifier, amplification of oscillation noise and resultant higher output voltage can be prevented. Consequently, power consumption by the amplifier can be reduced.

In the ultrasonic sensor as described above, the connection switching unit preferably has a potential control switch configured to switch the connection state between the potential controller and at least one of the receiver electrodes, and a short switch connected to each of the receiver electrodes and configured to switch the connection state between the receiver electrodes. In the first state, the connection switch portion is preferably configured to switch the short switch to a connection state in which the receiver electrodes are connected, and to switch the potential control switch to a connection state in which the potential controller is connected to at least one of the receiver electrodes.

According to this embodiment, during transmission periods, the short switch shorts the paired receiver electrodes and, additionally, the potential control switch connects the potential controller to the paired receiver electrodes, whereupon the potential controller respectively brings the paired receiver electrodes to the same potential at a first potential. The potential difference of the paired receiver electrodes is thereby brought to zero. Specifically, because it is sufficient to simply short the paired receiver electrodes, the configuration can be simplified.

Moreover, because the paired receiver electrodes are shorted by the short switch, the potential difference of the paired receiver electrodes can be reliably brought to zero, producing a state in which no electrical signal is output from the receiver electrodes.

In the ultrasonic sensor as described above, the potential controller preferably has a first potential controller configured to apply a voltage to one of the receiver electrodes, and a second potential controller configured to apply a voltage to the other of the receiver electrodes. The connection switching unit preferably has a first switch configured to switch the connection state between the first potential controller and the one of the receiver electrodes, and a second switch configured to switch the connection state between the second potential controller and the other of the receiver electrodes. In the first state, the connection switching unit is preferably configured to switch the first switch to a connection state in which the first potential controller and the one of the receiver electrodes are connected, and to switch the second switch to a connection state in which the second potential controller and the other of the receiver electrodes are connected.

According to this embodiment, during transmission periods, the connection switching unit switches the first switch to a connection state in which the first potential controller and one receiver electrode are connected, and additionally switches the second switch to a connection state in which the second potential controller and the other receiver electrode are connected. Therefore, the paired receiver electrodes and the first and second potential controllers are connected, respectively bringing the paired receiver electrodes to the same potential at a first potential. Therefore, the potential difference of the paired receiver electrodes is zero, and no electrical signal is output from the receiver electrodes. By so doing, during intervals in which the transmission film of the transmitter elements is oscillating, no electrical signal is output from the receiver electrodes, even if oscillation noise from the transmitter elements reaches the receiver elements. Consequently, oscillation noise produced by oscillation of the transmitter elements is not detected.

During the reception period following completion of a transmission period, on the other hand, the connection switching unit switches to the second state as described above. Therefore, the receiver elements can receive only the ultrasound received signals, and the sensing accuracy of the ultrasonic received signal can be enhanced.

The ultrasonic sensor as described above preferably further includes a trigger signal generator configured to output a trigger signal at least during the transmission period, and an actuation controller configured to output an actuation signal applied to the actuation electrodes of the transmitter element while simultaneously activating the trigger signal generator. The connection switching unit is preferably configured to switch to the first state upon input of the trigger signal from the trigger signal generator, and to switch to the second state upon termination of input of the trigger signal.

According to this embodiment, the actuation controller outputs an actuation signal applied to paired actuation electrodes of the transmitter elements, while simultaneously activating the trigger signal generator. By so doing, the trigger signal generator is prompted to output a trigger signal. Subsequently, the connection switching unit, upon input of the trigger signal, switches to the first state; and upon termination of input of the trigger signal switches to the second state. Therefore, while the actuation controller is outputting an actuation signal to the transmitter elements, the connection switching unit can be reliably switched to the first state, and the potential difference of the paired receiver electrodes can be brought to zero. Consequently, during the transmission period, no electrical signal is output from the receiver electrodes, and oscillation noise produced by oscillation of the transmitter elements is not detected. During the reception period following completion of the transmission period, on the other hand, as described previously, the receiver elements can receive only the ultrasound received signals, and the sensing accuracy of the ultrasonic received signal can be enhanced.

In the ultrasonic sensor as described above, the trigger signal generator is preferably configured to output the trigger signal in a trigger output period equivalent to at least one cycle of the actuation signal, plus the transmission period.

According to this embodiment, the trigger output period is set to an interval equivalent to at least one cycle of the ultrasonic actuation signal transmitted by the transmitter element, plus the transmission period.

There are instances in which oscillation noise generated during the ultrasound transmission period reaches the receiver elements after the transmission period has elapsed. According to the present invention, the trigger signal continues to be output even after the transmission period has elapsed, and the potential difference of the paired receiver electrodes remains at zero, whereby even if oscillation noise reaches the receiver elements after the transmission period has elapsed, the receiver elements do not output the oscillation noise as a received signal. Consequently, the sensing accuracy of the ultrasonic received signal by the receiver elements can be enhanced.

The electronic device according to another embodiment includes the ultrasonic sensor described above.

According to this embodiment, by providing the ultrasonic sensor described above, there may be realized electronic devices with enhanced sensing accuracy of the ultrasonic received signals as discussed above.

Whereas the prior art relied on providing an oscillation isolation member discussed above, according to the present invention, the necessity of providing such an oscillation isolation member is obviated, and accordingly the configuration can be simplified, making possible application in devices requiring compact size, such as biological testing devices, for example.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic sensor comprising:
a substrate;
a transmitter element formed above the substrate, the transmitter element including a transmission film adapted to transmit ultrasound through oscillation, a transmission piezoelectric body configured to cause the transmission film to oscillate, and a pair of actuation electrodes configured to apply an actuation voltage to the transmission piezoelectric body;
a receiver element that is formed above the substrate and different from the transmitter element, the receiver element including a reception film adapted to oscillate through reception of the ultrasound, a reception piezoelectric body configured to convert oscillation of the reception film to an electrical signal, and a pair of receiver electrodes configured to pick up the electrical signal that is output from the reception piezoelectric body;
a potential controller configured to apply a first potential to one of the pair of receiver electrodes, the first potential being negative voltage;
an actuation controller configured to output an actuation signal to one of the pair of actuation electrodes such that the pair of actuation electrodes apply the actuation voltage to the transmission piezoelectric body and the transmission film oscillates to transmit the ultrasound at the transmitter element;
a receiver amplifier connected to each of the pair of receiver electrodes;
a potential control switch configured to switch a state of connection between the one of the pair of receiver electrodes and the potential controller between a connection state in which the potential controller and the one of the pair of receiver electrodes are electrically connected to each other and a disconnected state in which the potential controller and the one of the pair of receiver electrodes are electrically disconnected; and
a short switch connected to each of the pair of receiver electrodes and configured to switch a state of connection between the pair of receiver electrodes between a connection state in which the pair of receiver electrodes are electrically connected to each other and a disconnected state in which the pair of receiver electrodes are electrically disconnected,
wherein during a transmission period in which the transmitter element transmits the ultrasound through the oscillation, while the actuation controller is outputting the actuation signal to the one of the pair of actuation electrodes, the potential control switch is in the connection state, the short switch is in the connection state, and the potential controller is applying the negative voltage to the one of the pair of receiver electrodes, such that the pair of receiver electrodes are shorted to each other and both of the pair of receiver electrodes have a same voltage which is the negative voltage, and
during a reception period in which the ultrasound is received by the reception element, the potential control switch is in the disconnected state, and the short switch is in the disconnected state.

2. A biological testing device comprises:
the ultrasonic sensor according to claim 1; and
a band configured to attach the ultrasonic sensor to a human body.

3. An ultrasonic sensor comprising:
a substrate;
a transmitter element formed above the substrate, the transmitter element including a transmission film adapted to transmit ultrasound through oscillation, a transmission piezoelectric body configured to cause the transmission film to oscillate, and a pair of actuation electrodes configured to apply an actuation voltage to the transmission piezoelectric body;
a receiver element that is formed above the substrate and different from the transmitter element, the receiver element including a reception film adapted to oscillate through reception of the ultrasound, a reception piezoelectric body configured to convert oscillation of the reception film to an electrical signal, and a pair of receiver electrodes configured to pick up the electrical signal that is output from the reception piezoelectric body;
a receiver amplifier connected to each of the pair of receiver electrodes;
an actuation controller configured to output an actuation signal to one of the pair of actuation electrodes such that the pair of actuation electrodes apply the actuation voltage to the transmission piezoelectric body and the transmission film oscillates to transmit the ultrasound at the transmitter element;
a first potential controller configured to apply negative voltage to one of the pair of receiver electrodes;
a second potential controller configured to apply the negative voltage to the other of the pair of receiver electrodes; and
a connection switch configured to switch a state of connection of the pair of receiver electrodes, the connection switch having a first switch configured to switch a state of connection between the first potential controller and the one of the pair of receiver electrodes between a connection state in which the first potential controller and the one of the pair of receiver electrodes are electrically connected to each other and a disconnected state in which the first potential controller and the one of the pair of receiver electrodes are electrically disconnected, and a second switch configured to switch a state of connection between the second potential controller and the other of the pair of receiver electrodes between a connection state in which the second potential controller and the other of the pair of receiver electrodes are electrically connected to each other and a disconnected state in which the second potential controller and the other of the pair of receiver electrodes are electrically disconnected,
wherein during a transmission period in which the transmitter element transmits the ultrasound through the oscillation, while the actuation controller is outputting the actuation signal to the one of the pair of actuation electrodes, the first switch is in the connection state, the second switch is in the connection state, the first potential controller is applying the negative voltage to the one of the pair of receiver electrodes, and the second potential controller is applying the negative voltage to the other of the pair of receiver electrodes, such that both of the one and the other of the pair of receiver electrodes have a same voltage which is the negative voltage, and during a reception period in which the ultrasound is received by the reception element, the first switch is in the disconnected state and the second switch is in the disconnection state.

4. A biological testing device comprises:
the ultrasonic sensor according to claim 3; and
a band configured to attach the ultrasonic sensor to a human body.

5. An ultrasonic sensor comprising:
a substrate having a plurality of opening portions;
a support film covering the opening portions;
a first piezoelectric element formed above the support film and in the inside region of a first opening portion among the opening portions in plan view, the first piezoelectric element including a piezoelectric body and a pair of first piezoelectric element electrodes connected to the piezoelectric body;
a second piezoelectric element formed above the support film and in the inside region of a second opening portion among the opening portions in plan view, the second piezoelectric element being different from the first piezoelectric element;
a potential controller configured to supply negative potential; and
a connection switch configured to switch a state of connection of the pair of first piezoelectric element electrodes and the potential controller between a connection state in which the potential controller and the pair of first piezoelectric element electrodes are electrically connected to each other and a disconnected state in which the potential controller and the pair of first piezoelectric element electrodes are electrically disconnected,
an actuation controller configured to output an actuation signal to the second piezoelectric element such that the support film under the second piezoelectric element oscillates to transmit ultrasound;
wherein during at least a part of duration of a transmission period in which the actuation signal is being applied to the second piezoelectric element and the support film under the second piezoelectric element is being oscillated to transmit the ultrasound through oscillation of the support film, while the actuation controller is outputting the actuation signal to the second piezoelectric element, the connection switch is in the connection state, and the potential controller is applying the negative voltage to the pair of first piezoelectric element electrodes, such that both of the pair of first piezoelectric element electrodes have a same voltage which is the negative voltage, and
during at least part of duration of a reception period in which an electrical signal of the first piezoelectric element is picked up, the connection switch is in the disconnect state.

6. A biological testing device comprises:
the ultrasonic sensor according to claim 5; and
a band configured to attach the ultrasonic sensor to a human body.

* * * * *